United States Patent [19]
Teichmüller et al.

[11] Patent Number: 5,866,559
[45] Date of Patent: Feb. 2, 1999

[54] 17α-CYANOMETHYLESTRA-4,9-DIEN DERIVATIVES AND PHARMACEUTICAL COMPOSITIONS CONTAINING SAME

[75] Inventors: Gerhard Teichmüller; Gerd Müller; Sigfrid Schwarz; Bernd Undeutsch, all of Jena; Harry Henkel, Apolda; Ronald Gebühr; Günter Kaufmann, both of Jena; Doris Hübler, Scheiden; Michael Oettel, Jena, all of Germany

[73] Assignee: Jenapharm GmbH, Jena, Germany

[21] Appl. No.: 771,805

[22] Filed: Dec. 20, 1996

[30]    Foreign Application Priority Data

Dec. 22, 1995  [DE]  Germany .......................... 195 48 449.5
Dec. 22, 1995  [DE]  Germany .......................... 195 48 450.9

[51] Int. Cl.$^6$ ................. A61K 31/57; C07J 7/00
[52] U.S. Cl. ............................................. 514/181; 550/598
[58] Field of Search ............................ 552/598; 514/171, 514/177, 181

[56]    References Cited

FOREIGN PATENT DOCUMENTS

24718872C2   12/1977   Germany .
WO 95/04536   2/1995   WIPO .

OTHER PUBLICATIONS

Croxatto, H. B. et al., "Female contraception and male fertility Regulation", ed. by Runnebaum, Rabe & Kiesel, vol. 2, Advances in Gynecological and Obstetric Research Series, p. 241, 1991.

*Primary Examiner*—José G. Dees
*Assistant Examiner*—Barbara Badeio
*Attorney, Agent, or Firm*—Michael J. Striker

[57] ABSTRACT

The 17α-cyanomethylestra-4,9-diene derivative compounds are of formula I:

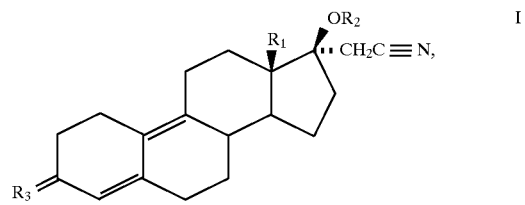

wherein $R_1$ is an alkyl group having from 1 to 2 carbon atoms; $R_2$ is an alkyl group with 1 to 10 carbon atoms, an acyl group with 1 to 10 carbon atoms or a trialkylsilyl group; and $R_3$ is an oxygen atom or a R—O—N group, wherein R is a hydrogen atom, an acyl group with 1 to 10 carbon atoms, an alkyl group with 1 to 10 carbon atoms, a sulfamoyl group, an alkylsilyl group or a trialkylsilyl group. These compounds, particularly in combination with at least one suitable estrogen, are suitable for treatment of endometrioses or gestagen-dependent tumors and for hormonal contraception and climacteric hormone replacement therapy (HRT). Processes for making the new steroids are described as well as methods of making the pharmaceutical compositions containing them.

5 Claims, No Drawings

17α-CYANOMETHYLESTRA-4,9-DIEN DERIVATIVES AND PHARMACEUTICAL COMPOSITIONS CONTAINING SAME

BACKGROUND OF THE INVENTION

The present invention relates to certain new 17α-cyanomethylestra-4,9-diene derivative compounds.

17α-cyanomethyl-17β-hydroxyestra-4,9-dien-3-one (DIENOGEST) is known from the professional and patent literature. This compounds is described in German Published Patent Application DE 27 18 872.

SUMMARY OF THE INVENTION

It is an object of the invention to provide new 17α-cyanomethylestra-4,9-diene derivative compounds as well as processes for making them.

According to the invention, the 17α-cyanomethylestra-4,9-diene derivative compounds of the general formula I:

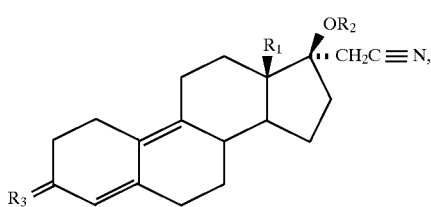

wherein $R_1$ is an alkyl group having from 1 to 2 carbon atoms, $R_2$ is an alkyl group with 1 to 10 carbon atoms, an acyl group with 1 to 10 carbon atoms or a trialkylsilyl group, and $R_3$ is an oxygen atom or a R—O—N group, in which R is a hydrogen atom, an acyl group with 1 to 10 carbon atoms, an alkyl group with 1 to 10 carbon atoms, a sulfamoyl group, an alkylsilyl group or a trialkylsilyl group, are new compounds, whose preparation and biological activity have not been described up to now.

Preferred 17α-cyanomethylestra-4,9-diene derivative compounds of the formula I are for example:
17α-cyanomethylestra-4,9-dien-3-on-17β-yl-acetate,
17α-cyanomethylestra-4,9-dien-3-on-17β-yl-propionate,
17α-cyanomethylestra-4,9-dien-3-on-17β-yl-butyrate,
17α-cyanomethylestra-4,9-dien-3-on-17β-yl-isobutyrate,
17α-cyanomethylestra-4,9-dien-3-on-17β-yl-valerate,
17α-cyanomethylestra-4,9-dien-3-on-17β-yl-isovalerate,
17α-cyanomethylestra-4,9-dien-3-on-17β-yl-decanoate,
17α-cyanomethylestra-4,9-dien-3-on-17β-yl-cyclohexanoate
17α-cyanomethylestra-4,9-dien-3-on-17β-yl-benzoate,
17α-cyanomethylestra-4,9-dien-3-on-17β-yl-methylcarbonate,
17α-cyanomethylestra-4,9-dien-3-on-17β-yl-ethylcarbamate,
17α-cyanomethylestra-4,9-dien-3-on-17β-yl-dimethylcarbamate,
17α-cyanomethylestra-4,9-dien-3-on-17β-yl-phenylcarbamate,
17α-cyanomethyl-17β-trimethylsilyloxyestra-4,9-dien-3-one,
17α-cyanomethyl-17β-triethylsilyloxyestra-4,9-dien-3-one,
17α-cyanomethyl-17β-dimethyl-t-butylsilyloxyestra-4,9-dien-3-one,
17α-cyanomethyl-17β-ethoxyethoxyestra-4,9-dien-3-one,
17α-cyanomethyl-17β-tetrahydropyranyloxyestra-4,9-dien-3-one,
17α-cyanomethyl-3-hydroxyiminoestra-4,9-dien-17β-yl-acetate,
17α-cyanomethyl-3-hydroxyiminoestra-4,9-dien-17β-yl-propionate,
17α-cyanomethyl-3-hydroxyiminoestra-4,9-dien-17β-yl-butyrate,
17α-cyanomethyl-3-hydroxyiminoestra-4,9-dien-17β-yl-valerate,
17α-cyanomethyl-3-hydroxyiminoestra-4,9-dien-17β-yl-cyclopentanoate,
17α-cyanomethyl-3-hydroxyiminoestra-4,9-dien-17β-yl-methyl-carbonate,
17α-cyanomethyl-3-hydroxyiminoestra-4,9-dien-17β-yl-ethyl-carbamate,
17α-cyanomethyl-3-hydroxyiminoestra-4,9-dien-17β-yl-dimethylcarbamate,
17α-cyanomethyl-3-hydroxyiminoestra-4,9-dien-17β-yl-benzoate,
17α-cyanomethyl-3-hydroxyiminoestra-4,9-dien-17β-yl-decanoate,
3-acetoxyimino-17α-cyanomethylestra-4,9-dien-17β-yl-acetate,
3-acetoxyimino-17α-cyanomethylestra-4,9-dien-17β-yl-valerate,
3-acetoxyimino-17α-cyanomethylestra-4,9-dien-17β-yl-benzoate,
3-acetoxyimino-17α-cyanomethylestra-4,9-dien-17β-yl-phenylcarbamate,
3-acetoxyimino-17α-cyanomethylestra-4,9-dien-17β-yl-methyl-carbonate,
17α-cyanomethyl-3-propionyloxyimino-estra-4,9-dien-17β-yl-acetate,
3-benzoyloxyimino-17α-cyanomethylestra-4,9-dien-17β-yl-acetate,
3-benzoyloxyimino-17α-cyanomethylestra-4,9-dien-17β-yl-benzoate,
17α-cyanomethyl-3-(N-phenyl)carbamoyloxyimino-estra-4,9-dien-17β-yl-acetate,
17α-cyanomethyl-3-(methoxycarbonyloxy)imino-estra-4,9-dien-17β-yl-acetate,
3-tert-butoxyimino-17α-cyanomethyl-estra-4,9-dien-17β-yl-acetate,
3-tert-butoxyimino-17α-cyanomethyl-estra-4,9-dien-17β-yl-benzoate,
3-tert-butoxyimino-17α-cyanomethyl-estra-4,9-dien-17β-yl-phenylcarbamate,
3-tert-butoxyimino-17α-cyanomethyl-estra-4,9-dien-17β-yl-methylcarbonate,
3-cyanoethoxyimino-17α-cyanomethyl-estra-4,9-dien-17β-yl-acetate,
3-cyanoethoxyimino-17α-cyanomethyl-estra-4,9-dien-17β-yl-valerate,
3-cyanoethoxyimino-17α-cyanomethyl-estra-4,9-dien-17β-yl-decanoate,
3-cyanoethoxyimino-17α-cyanomethyl-estra-4,9-dien-17β-yl-methylcarbonate,
3-cyanoethoxyimino-17α-cyanomethyl-estra-4,9-dien-17β-yl-phenylcarbamate,
17α-cyanomethyl-3-(N,N-diethylsulfamoyloxy)imino-estra-4,9-dien-17β-yl-acetate,
17α-cyanomethyl-3-(N-acetylsulfamoyloxy)imino-estra-4,9-dien-17β-yl-valerianate.

Pharmaceutical compositions containing at least one 17α-cyano-methylestra-4,9-diene compound of the general formula I as the effective ingredient together with suitable carrier and adjuvant substances are also part of the invention.

The compounds according to the invention have a gestagen activity profile without undesirable side effects in comparison the conventional gestagens. They provide a comparatively strong gestagen activity without androgenic and anabolic group activity, but instead surprisingly have a significant anti-androgenic partial activity.

The outstanding compatiblity of the compounds according to the invention is particularly advantageous and they produce scarcely any undesirable side effects in comparison to conventional 17α-ethinyl-17β-hydroxysteroids, also at increased dosages.

The pharmacological experiments show that these new 17α-cyanomethyl-19-nor-gestagens have a substantially different activity profile than the conventional 17α-ethinyl-19-nor-gestagens.

Because of their specific hormonal and anti-hormonal partial activity the new substances are used for treatment of endocrine pathogens and reproductive control in human and veterinary medicine.

Furthermore the compounds according to the invention are used alone or in combination with estrogens in the form of multi-step or combination preparations for hormonal contraception because of their gestagen activity The gestagen and estrogen effective ingredients are preferably taken together orally in preparations for contraception. Synthetic estrogens, preferably from the ethinylestradiol group, mestranol group and biogenic estrogens, particularly from the estradiol group, the estrone group and estratriol group, may be used as the estrogen active ingredient.

The compounds according to the invention can also be used in preparations for treatment of gynecological problems and for substitution therapy. The new compounds are suitable for treatment of premenstrual complaints because of their activity profile.

Furthermore the pharmaceutical compositions containing the compounds according to the invention can be used for treatment of endometrioses and for therapy of gestagen-dependent tumors.

The medications of the invention are prepared in a conventional solid or liquid carrier or diluent and a conventional pharmaceutically-made adjuvant at suitable dosage level in a known way. The preferred preparations are in administratable form which is suitable for oral application. These administratable forms, for example, include pills, tablets, film tablets, coated tablets, capsules, powders and deposits.

It is also possible to work the new compounds into suspensions or solutions.

Transdermal systems can also be used to administer the compounds according to the invention.

The compounds according to the invention can also be used as gestagen ingredients in compositions for female fertility control, which are marked by the additional use of a competitive progesterone antagonist (H. B. Croxatto et al, "Female Contraception and Male Fertility Regulation", ed. by Runnebaum, Rabe & Kiesel, Vol. 2, Advances in Gynecological and Obstetric Research Series, Parthenon Publishing Group, p. 241, 1991). The additional, competitive progesterone antagonist can also be applied sequentially.

The compounds according to the invention can be used to prepare intermediate products for synthesis of additional pharmacologically highly effective steroid products.

The synthesis of the compounds according to the invention occurs in a known way according to the appended process claims and in the following manner.

The compounds of the general formula II:

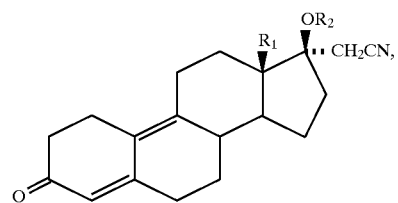

in which $R_1$ is an alkyl group with one to two carbon atoms, and $R_2$ is a hydrogen atom, are esterified in the presence of an amine with an acid or an acid derivative, such as an acid anhydride or an acid halide, in the presence of a catalyst, for example dimethylaminopyridine, to form the compounds of formula I. This reaction is advantageously performed with heating under a protective gas atmosphere. The reaction product is isolated by precipitation in ice water and separation of the solid product or by extraction with a suitable solvent. The use of inert solvents, which essentially improve the solubility of the starting materials, is not prohibited. This type of solvent may advantageously be those suitable for extraction processes, for example, halogenated hydrocarbons, acetic acid esters and ethers, such as t-butyl methyl ether, among others.

For synthesis of the new substances also compounds of the formula II above, in which $R_1$ is an alkyl group with one to two carbon atoms and $R_2$ is a hydrogen atom, are converted with alkyl- or arylisocyanates in the presence of amines in an inert solvent at elevated reaction temperatures to the compounds of the formula I.

In an additional possible synthetic route, e.g., 17α-cyanomethyl-17β-hydroxy-estra-4,9-dien-3-one (DIENOGEST), is esterified with an alkenoylacylate, such as isopropenylacetate, to form a compound of the general formula III:

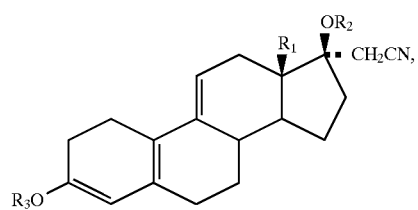

in which $R_1$ is an alkyl group with one to two carbon atoms and $R_2$ and $R_3$ means an acyl group with 1 to 10 carbon atoms. The compound of formula III isolated and then converted to the compounds according to the invention in an aqueous organic solvent in the presence of an acid, such as hydrochloric acid, sulfuric acid, toluene sulfonic acid at elevated reaction temperatures. The compounds according to the invention are then isolated by precipitation or extraction.

Additional embodiments of the synthesis process for making the compounds of formula I include converting compounds of the general formula IV:

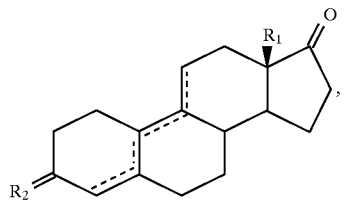

in which $R_1$ is an alkyl group with one to two carbon atoms and $R_2$ is an oxyimino- , dimethoxy- , ethylenedioxy- or 2,2-dimethyl-1,3-propylenedioxy group, in a known way by reaction with lithium acetonitrile to the 17α-cyanomethyl derivative of the general formula V, or converting the compounds of formula IV with trimethylsulfonium iodide to 17,17'-spiroepoxide, which then is converted to the compound of the general formula V:

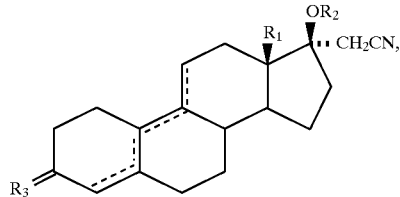

wherein $R_1$ is an alkyl group with one to two carbon atoms and $R_2$ is a hydrogen atom or a lithium atom, and $R_3$ is an an oxyimino-, dimethoxy-, ethylenedioxy- or 2,2-dimethyl-1,3-propylenedioxy group. This product is converted to the compound of the general formula V' by esterification:

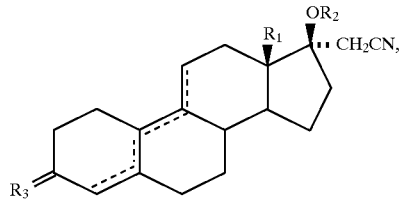

in which $R_1$ is an alkyl group with one to two carbon atoms, $R_2$ is an acyl group with 1 to 10 carbon atoms and $R_3$ is an acyloxyimino group with 1 to 10 carbon atoms, a dimethoxy, an ethylenedioxy- or a 2,2-dimethyl-1,3-propylenedioxy group. This latter product compound is subsequently converted into the compounds according to the invention by a ketal cleavage/acyloxyimino cleavage in aqueous organic solution, such as acetic acid, methanol or acetone, using a catalyst, for example hydrochloric acid, sulfuric acid, nitric acid, p-toluene sulfonic acid or pyruvic acid, in the presence of elevated temperatures.

The ether derivatives of the new substances are made from the compounds of the general formula II by reaction with an unsaturated ether, for example vinyl ether or dihydropyran, in an inert organic solvent in the presence of a catalyst such as pyridinium p-toluene sulfonate.

Trialkylsilylether derivatives of the new substances can be made from the compounds of the general formula II by reaction with a trialkylsilyl halide in the presence of an amine, for example pyridine or triethylamine, in an inert organic solvent. Advantageously a catalyst such as dimethylaminopyridine is added during this reaction.

Also the compounds of the general formula I':

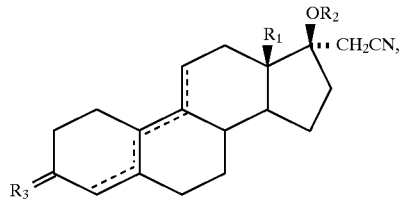

in which $R_1$ is an alkyl group with one to two carbon atoms, $R_2$ is an alkyl group or an acyl group with 1 to 10 carbon atoms or a trialkylsilyl group and $R_3$ is an oxygen atom, react in a known way with hydroxylammonium chloride in an amine, or in an inert solvent with addition of an acid binding agent, and the hydroxyimino steroid derivative in which $R_1$ and $R_2$ have the same meaning as above and $R_3$ is a hydroxyimino group is isolated. This isolated derivative is converted in a known way with an acid derivative, such as a carboxylic acid anhydride, a carboxylic acid halide, e.g. a carboxylic acid chloride, or a sulfamoyl halide, e.g. sulfamoyl chloride, in an amine, or in an inert solvent with addition of an amine, and the acyloxyimino derivative or the sulfamoyloxyimino derivative, in which $R_1$ and $R_2$ have the same meaning as above and $R_3$ is an acyloxyimino- or sulfamoyloxyimino group, is isolated. Alternatively, the hydroxyimino derivative formed in the manner described hereinabove is reacted in a known way with alkyl or arylisocyanates or alkylchloroformates in an inert organic solvent in the presence of an amine and the resulting alkylcarbamoyloxyimino-, arylcarbamoyloxyimino- or alkyloxycarbonyloxyimino derivative, in which $R_1$ and $R_2$ have the same meaning as above and $R_3$ is an alkylcarbamoyloxyimino- or arylcarbamoyloxyimino group or an alkyloxycarbonyloxyimino group, is isolated. The hydroxyimino products are converted in a known way into an alkyloxyimino derivative and/or trialkylsilyloxyimino derivative, in which $R_1$ and $R_2$ have the same meaning as above and $R_3$ is an alkyloxyimino- or trialkyl-silyloxyimino group, with alkenes, e.g. isobutylene, or unsatured ethers, e.g. vinyl ether or dihydropyran, in an inert organic solvent with addition of catalysts, such as pyridinium-p-toluene sulfonate or with trialkylsilyl halides, such as triethylsilyl bromide, in an inert organic solvent with addition of an amine.

An additional embodiment of the process for making the compounds of the general formula I comprises reacting in a known way the compound of the general formula VI:

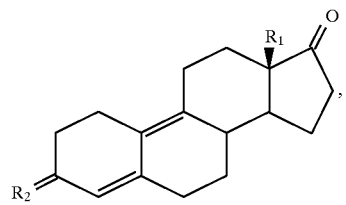

in which $R_1$ is an alkyl group with one to two carbon atoms and $R_2$ is a hydroxyimino group, with lithium acetonitrile or with trimethylsulfonium iodide, and subsequently treating with an alkali cyanide to form the compounds of the general formula I, in which $R_1$ is an alkyl group having from 1 to 2 carbon atoms, $R_2$ is a hydrogen atom and $R_3$ is a hydroxyimino group instead of an oxygen atom. This reacts in a known way with an acid derivative, e.g. carboxylic anhydride or carboxylic acid halide, in an amine, or in an inert solvent with addition of an amine, and the acyl derivative, in which $R_1$ has the above-described significance, $R_2$ is an acyl group and $R_3$ is an acyloxyimino group, is isolated. Alternatively, the hydroxyimino product is reacted in a known way with alkyl- or arylisocyanates or alkylchloroformates in an inert organic solvent in the presence of an amine and the resulting alkylcarbamoyl-, arylcarbamoyl- or alkyloxycarbonyl derivative, in which $R_1$ has the above-described significance, $R_2$ is an alkylcarbamoyl-, arylcarbamoyl- or alkyloxycarbonyl group and $R_3$ is an alkylcarbamoylimino group or arylcarbamoylimino group, is isolated. Alternatively, the hydroxyimino product is converted into an alkyl derivative or trialkylsilyl derivative, in which $R_1$ has the above-described significance, $R_2$ is an alkyl or trialkyl group and $R_3$ is an alkyloxyimino- or trialkylsilyloxyimino group, in a known way by reacting with alkenes, e.g. isobutylene, or unsatured ethers, e.g. vinyl ether or dihydropyran, in an inert organic solvent with addition of catalyst, such as pyridinium p-toluene sulfonates, or by reacting with trialkylsilyl halides, e.g. triethylsilyl bromides, in an inert organic solvent, with addition of an amine.

The pharmaceutical preparations, which contain at least one of the 17α-cyanomethylestra-4,9-diene derivative compounds of formula I, include pharmaceutically compatible carrier and auxiliary substances if necessary.

The process of making the compounds according to the invention of the formula I is illustrated in the following examples, however the appended claims are not to be considered limited further by these examples.

EXAMPLES

Example 1
17α-cyanomethyl-3-hydroxyiminoestra-4,9-dien-17β-yl-acetate 5.0 g of 17α-cyanomethyl-estra-4,9-dien-17β-yl-acetate are mixed with 2.5 g of hydroxylammonium hydrochloride in 25 ml of pyridine. After one hour reaction time at 35° C. 1 liter of ice water is added to the reaction mixture with stirring and the resulting precipitate is separated by vacuum filtration, washed with water and dried. The crude product is recrystallized from methanol, chromatographed over silica gel in $CH_2Cl_2$ and recrystallized again from methanol. The yield was 2.3 g.

Example 2
17α-cyanomethyl-3-hydroxyiminoestra-4,9-dien-17β-yl-propionate 3.5 g of 17α-cyanomethyl-estra-4,9-dien-17β-yl-propionate is mixed with 875 mg hydroxylammonium chloride in 17.5 ml pyridine. The reaction was completed after 2.5 hours reaction time at 35° C. The reaction mixture is mixed with 750 ml of ice water with stirring to form a precipitate, filtered with suction and the precipitate is washed. The crude product is recrystallized from methylene chloride/methanol solvent, the crystal product isolated by filtration with suction, washed with methanol and dried. The yield is 3.08 g.

Example 3
3-acetyloxyimino-17α-cyanomethyl-estra-4,9-dien-17β-yl-acetate 2 g of 17α-cyanomethyl-3-hydroxyiminoestra-4,9-dien-17β-yl-acetate are reacted with 8 ml of acetic anhydride and 100 mg of dimethylaminopyridine in 8 ml of pyridine. The reaction was completed after 1 hour at 40° C. The isolation of the product occurs by precipitation in ice water and recrystallization from methanol.

Example 4
17α-cyanomethyl-3-valeroyloxyiminoestra-4,9-dien-17β-yl-acetate 1.5 g of 17α-cyanomethyl-3-hydroxyiminoestra-4,9-dien-17β-yl-acetate are completely reacted in one hour at 45° C. in 6 ml pyridine and 6 ml valeric acid anhydride on addition of 75 mg of dimethylaminopyridine. Subsequently the reaction mixture is added to ice water, extracted with methylene chloride, washed with an acid-free solvent and evaporated until a solid product is formed.

Example 5
17α-cyanomethyl-3-phenylcarbamoyloxyiminoestra-4,9-dien-17β-yl-acetate 1.5 g of 17α-cyanomethyl-3-hydroxyiminoestra-4,9-dien-17β-yl-acetate are mixed with 0.6 ml phenyl isocyanate in 40 ml toluene and 2 ml triethylamine with stirring at room temperature. After the reaction is completed the mixture is mixed with 5 ml of methanol and then with 50 ml water, extracted with toluene, the solution is washed with water, concentrated and the residue is crystallized from methylene chloride/methanol. The product melting point was 170° to 188° C. and the yield was 1.6 g.

Example 6
17α-cyanomethyl-3-methoxycarboxylyoxyiminoestra-4,9-dien-17β-yl-acetate 2 g of 17α-cyanomethyl-3-hydroxyiminoestra-4,9-dien-17β-yl-acetate are dissolved in 10 ml pyridine, the solution is cooled to −5° C. and then mixed with stirring with a solution of 0.82 ml of methylchloroformate in 20 ml of toluene. After one hour reaction time at room temperature the reaction is completed. The reaction mixture was decomposed by addition of 5 ml of methanol and then with 50 ml of water, extracted with toluene. The resulting extract was washed with water, concentrated and the resulting residue was recrystallized from methanol. The product melting point was 126° to 132° C. and the yield was 1.42 g.

Example 7
3-benzoyloxy-17α-cyanomethyl-estra-4,9-dien-17β-yl-acetate 2 g of 17α-cyanomethyl-3-hydroxyiminoestra-4,9-dien-17β-yl-acetate are dissolved in 10 ml pyridine and mixed with 1.2 ml of benzoyl chloride with stirring at room temperature, whereby the temperature increases until at at 35° C. The reaction was completed after 15 minutes reaction time. The reaction mixture was stirred into ice water and extracted with methylene chloride. The resulting product was subjected to a vacuum filtration, washed with water and then recrystallized from methylene chloride/methanol. The product melting point was 190° to 215° C. and the yield was 2.24 g.

Example 8
17α-cyanomethyl-3-N,N-dimethylcarbamoyloxyiminoestra-4,9-dien-17β-yl-acetate 2 g of 17α-cyanomethyl-3-hydroxyiminoestra-4,9-dien-17β-yl-acetate are dissolved in 10 ml pyridine, the solution is cooled to −6° C. and mixed with a solution of 0.75 ml N,N-dimethylcarbamoyl chloride in 20 ml of toluene with stirring. After a 5 hour reaction time at 50° C. the reaction was completed. The reaction mixture was decomposed by addition of 5 ml of methanol and 25 ml of water. The toluene solution was separated, concentrated and the residue was crystallized from methanol. The product melting point was 97° to 110° C. and the yield was 1.35 g.

Example 9
17α-cyanomethyl,-estra-4,9-dien-3-on-17β-yl-acetate 10 g of 17α-cyanomethyl-estra-4,9-dien-3-on-17β-ol, 50 ml pyridine, 50 ml acetic anhydride and 500 mg of dimethylaminopyridine are heated up to 80° C. in an inert gas atmosphere with stirring. After complete reaction (DC control) the reaction mixture is cooled and poured with stirring into ice water. The precipitate is filtered with suction, washed well with water, dried and then dissolved in methylene chloride. That solution is mixed with methanol and concentrated under vacuum until crystallization begins. The crystallate is subjected to vacuum filtration, washed with cold methanol and dried.

Example 10
17α-cyanomethyl-estra-4,9-dien-3-on-17β-yl-propionate 10 g of 17α-cyanomethyl-estra-4,9-dien-3-on-17β-ol, 50 ml pyridine, 50 ml propionic acid anhydride and 500 mg of dimethylaminopyridine are heated up to 80° C. in an inert gas atmosphere with stirring. After complete reaction (DC control) the reaction mixture is cooled and poured with stirring into ice water. The precipitate is filtered with suction, washed well with water, dried and then dissolved in methylene chloride. That solution is mixed with methanol and concentrated under vacuum until crystallization begins. The crystallate is subjected to vacuum filtration, washed with cold methanol and dried.

Example 11
17α-cyanomethyl-estra-4,9-dien-3-on-17β-yl-valerate 5 g of 17α-cyanomethyl-estra-4,9-dien-3-on-17β-ol, 20 ml pyridine, 20 ml valeric acid anhydride and 250 mg of 4-(dimethylamino)pyridine are heated with stirring up to 96° C. The reaction is halted after 5 hours at this temperature, then cooled and poured with stirring into 1 liter of ice water. The solid product is subjected to a vacuum filtration, washed and dried. The yield of crude product was 6.3 g. This product was recrystallized from methanol to obtain 4.8 g of crystalline product. Chromatography of the recrystallized product was performed over silica gel in methylene chloride solution and the pure product was crystallized from methanol. The product melting point was 152° to 155° C. and the yield was 2.0 g.

Example 12
17α-cyanomethyl-estra-4,9-dien-3-on-17β-yl-(N-phenyl) carbamate 4.66 g 17α-cyanomethyl-estra-4,9-dien-3-on-17β-ol, 20 ml pyridine and 80 ml toluene are prepared and mixed with stirring with 2 ml phenyl isocyanate. The mixture was heated to 80° C., then mixed with another 2 ml phenyl isocyanate and stopped after an additional 6 hours at these conditions. After successful conversion it is cooled, reacted with methanol and added to water. The product is extracted with toluene, the extract is washed with water, dried and concentrated in a rotary vacuum evaporator. The residue is crystallized with methanol. Additional recrystallization from methanol results in a pure product.

The subject matter of corresponding German Patent Applications 195 48 449.5-43 and 195 48 450.9 of Dec. 22, 1995 is incorporated here by references. A claim of priority under 35 U.S.C 119 for the instant invention is based on both these German Patent Applications which disclose the same subject matter as the instant invention.

While the invention has been illustrated and described as embodied in 17α-cyanomethylestra-4,9-diene derivative compounds, processes for making same and pharmaceutical compositions containing same, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

What is claimed is:

1. A 17α-cyanomethylestra-4,9-diene derivative compound of formula I:

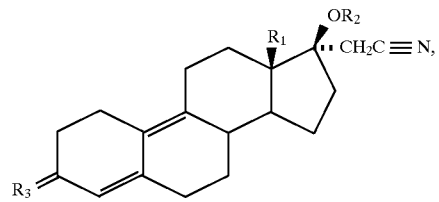

in which
  $R_1$ is an alkyl group having from 1 to 2 carbon atoms;
  $R_2$ is an acyl group with 1 to 10 carbon atoms; and
  $R_3$ is an oxygen atom.

2. A 17α-cyanomethylestra-4,9-diene derivative compound selected from the group consisting of
  17α-cyanomethylestra-4,9-dien-3-on-17β-yl-acetate,
  17α-cyanomethylestra-4,9-dien-3-on-17β-yl-propionate,
  17α-cyanomethylestra-4,9-dien-3-on-17β-yl-butyrate,
  17α-cyanomethylestra-4,9-dien-3-on-17β-yl-isobutyrate,
  17α-cyanomethylestra-4,9-dien-3-on-17β-yl-valerate,
  17α-cyanomethylestra-4,9-dien-3-on-17β-yl-isovalerate,
  17α-cyanomethylestra-4,9-dien-3-on-17β-yl-decanoate,
  17α-cyanomethylestra-4,9-dien-3-on-17β-yl-cyclohexanoate,
  17α-cyanomethylestra-4,9-dien-3-on-17β-yl-benzoate, and
  17α-cyanomethylestra-4,9-dien-3-on-17β-yl-methylcarbonate.

3. 17α-cyanomethylestra-4,9-dien-3-on-17β-yl-isobutyrate.

4. A pharmaceutical composition containing at least one 17α-cyanomethylestra-4,9-diene derivative compound and at least one pharmaceutically acceptable carrier, wherein said at least one 17α-cyanomethylestra-4,9-diene derivative compound has the formula I:

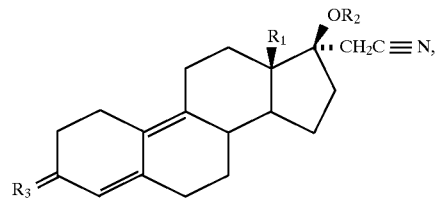

in which $R_1$ is an alkyl group having from 1 to 2 carbon atoms, $R_2$ is an acyl group with 1 to 10 carbon atoms and $R_3$ is an oxo group.

5. A pharmaceutical composition containing 17α-cyanomethyl-estra-4,9-dien-3-on-17β-yl-isobutyrate and at least one pharmaceutically acceptable carrier.

* * * * *